United States Patent

Bringmann et al.

[11] Patent Number: 5,260,315
[45] Date of Patent: Nov. 9, 1993

[54] USE OF DIONCOPHYLLINES AS FUNGICIDES

[75] Inventors: Gerhard Bringmann, Wuerzburg; Martin Ruebenacker, Altrip; Eberhard Ammermann, Ludwigshafen; Gisela Lorenz, Neustadt, all of Fed. Rep. of Germany; Laurent A. Assi, Abidjan, Ivory Coast

[73] Assignee: BASF Aktiengesellschaft, Ludwigshafen, Fed. Rep. of Germany

[21] Appl. No.: 887,933

[22] Filed: May 26, 1992

[30] Foreign Application Priority Data

May 25, 1991 [DE] Fed. Rep. of Germany ....... 4117080

[51] Int. Cl.$^5$ .............................. A01N 43/42
[52] U.S. Cl. ................................. 514/307
[58] Field of Search ......................... 514/307

[56] References Cited

PUBLICATIONS

The Alkaloids, vol. 29, 1986, pp. 141–186, G. Bringmann, "The Naphthyl Isoquinoline Alkaloids".

Primary Examiner—Allen J. Robinson
Attorney, Agent, or Firm—Oblon, Spivak, McClelland, Maier & Neustadt

[57] ABSTRACT

Methods for combating fungi using dioncophylline A or dioncophylline B.

3 Claims, No Drawings

USE OF DIONCOPHYLLINES AS FUNGICIDES

The present invention relates to the use of dioncophyllines, especially dioncophylline A and dioncophylline B, as fungicides, especially as fungicides in agriculture, i.e., for combating plant-pathogenic fungi.

Dioncophylline A has the following structural formula

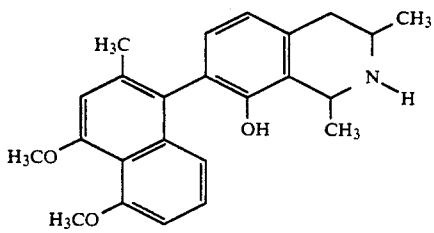

Dioncophylline B has the following structural formula

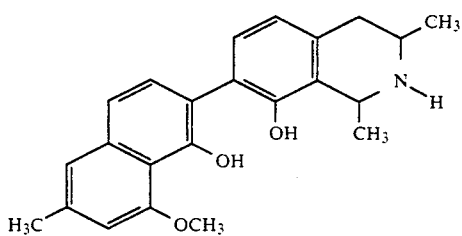

The compounds are disclosed in the periodical Planta Med. 56 (1990), pp. 495 and 496.

Dioncophylline A has the following physico-chemical values:

Melting point: 214° C.; $[\alpha]_D^{20} - 14.9$ (c=0.45; CHCl$_3$).

Dioncophylline B has the following physico-chemical values:

$[\alpha]_D^{20} - 37.6°$ (CHCl$_3$; c 0.37). IR $\nu_{max}$ cm$^{-1}$: 3375, 3280 (O—H), 2950, 2920 (C—H).

We have found that the two dioncophyllines mentioned above, and particularly dioncophylline B, have a good fungicidal action, which is especially evident on plant-pathogenic fungi.

Examples of such fungi are

| Fungus | Plants affected |
| --- | --- |
| Alternaria solani | potatoes, tomatoes |
| Botrytis cinerea | strawberries, grapes |
| Erysiphe cichoracearum | cucumbers |
| Erysiphe graminis | cereals |
| Fusarium culmorum | millet |
| Leptosphaeria nodorum | wheat |
| Mycosphaerella arachidicola | groundnuts |
| Plasmopara viticola | grapes |
| Puccinia recondita | wheat |
| Pyricularia oryzae | rice |
| Pyrenophora teres | barley |
| Pseudocercosporella herpotrichoides | wheat, barley |

The abovementioned compounds are suitable as fungicides.

The agents containing these compounds may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients or the seeds of the plants are treated with the active ingredients.

Formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acis with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, grapes, fruit and ornamentals in horticulture and viticulture, and in vegetables such as cucumbers, beans and cucurbits.

The compounds are applied by spraying or dusting the plants with the active ingredients, or treating the seeds of the plants with the active ingredients. They may be applied before or after infection of the plants or seeds by the fungi.

The compounds I are particularly useful for controlling the following plant diseases:
Erysiphe cichoracearum and Sphaerotheca fuliginea in cucurbits,
Podosphaera leucotricha in apples,
Uncinula necator in vines,
Puccinia species in cereals,
Rhizoctonia solani in cotton,
Ustilago species in cereals and sugar cane,
Venturia inaequalis (scab) in apples,
Helminthosporium species in cereals,
Septoria nodorum in wheat,
Cercospora arachidicola in groundnuts,
Phytophthora infestans in potatoes and tomatoes,
Fusarium and Verticillium species in various plants,
Alternaria species in fruit and vegetables.

The compounds may also be used for protecting materials (timber), e.g., against Paecilomyces variotii.

The fungicidal agents generally contain from 0.1 to 95, and preferably from 0.5 to 90, wt % of active ingredient.

The application rates depend on the effect desired, and vary from 0.02 to 3 kg of active ingredient per hectare.

When the active ingredients are used for treating seed, amounts of from 0.001 to 50, and preferably from 0.01 to 10, g per kg of seed are generally required.

When the agents are used as fungicides, they may also be applied together with other active ingredients, e.g., herbicides, insecticides, growth regulators, other fungicides and fertilizers.

When the agents are admixed with other fungicides, the fungicidal spectrum is in many cases increased.

USE EXAMPLE 1

Action on Botrytis cinerea

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

Assessment:
0 = no fungus attack, graduated down to
5 = total attack

| Active ingredient no. | Leaf attack in % after spraying with aqueous formulations containing 0.05% of active ingredient |
|---|---|
| Dioncophylline B | 0 |
| N-trichloromethylthio-tetrahydrophthalimide (prior art compound | 20 |
| Untreated | 65 |

USE EXAMPLE 2

Action on Plasmopara viticola

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

Assessment:
0 = no fungus attack, graduated to
5 = total attack

| Active ingredient no. | Leaf attack in % after spraying with aqueous formulations containing 250 ppm of active ingredient |
|---|---|
| Dioncophylline B | 5 |
| Untreated | 70 |

We claim:
1. A method of combatting fungi, wherein the fungi or the plants, seed, objects or soil threatened by fungus attack are treated with a fungicidally effective amount of a compound selected from the group consisting of dioncophylline A, dioncophylline B, and mixtures thereof.

2. A method according to claim 1, wherein said compound is dioncophylline A.

3. A method according to claim 1, wherein said compound is dioncophylline B.

* * * * *